(12) United States Patent
White

(10) Patent No.: US 11,510,870 B1
(45) Date of Patent: *Nov. 29, 2022

(54) SUBSTRATES FOR VAPORIZING AND DELIVERING AN AEROSOL

(71) Applicant: Jackie L. White, Pfafftown, NC (US)

(72) Inventor: Jackie L. White, Pfafftown, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 17/463,343

(22) Filed: Aug. 31, 2021

(51) Int. Cl.
*A61K 9/00* (2006.01)
*A61K 31/616* (2006.01)
*A61K 9/20* (2006.01)
*A24B 15/167* (2020.01)

(52) U.S. Cl.
CPC .......... *A61K 9/0073* (2013.01); *A24B 15/167* (2016.11); *A61K 9/2013* (2013.01); *A61K 9/2018* (2013.01); *A61K 9/2068* (2013.01); *A61K 9/2072* (2013.01); *A61K 31/616* (2013.01)

(58) Field of Classification Search
CPC .. A61K 9/0073; A61K 9/2013; A61K 9/2018; A61K 9/2068; A61K 9/2072; A61K 31/616
See application file for complete search history.

(56) References Cited

U.S. PATENT DOCUMENTS

| | | |
|---|---|---|
| 4,062,368 A | 12/1977 | Crellin |
| 4,596,259 A | 6/1986 | White et al. |
| 4,714,082 A | 12/1987 | Banerjee et al. |
| 4,756,318 A | 7/1988 | Clearman et al. |
| 4,771,795 A | 9/1988 | White et al. |
| 4,819,665 A | 4/1989 | Roberts et al. |
| 4,827,950 A | 5/1989 | Banerjee et al. |
| 4,836,225 A | 6/1989 | Sudoh |
| 4,893,639 A | 1/1990 | White |
| 4,913,169 A | 4/1990 | Templeton |
| 4,989,619 A | 2/1991 | Clearman |

(Continued)

FOREIGN PATENT DOCUMENTS

| | | |
|---|---|---|
| GB | 1501152 A | 2/1978 |
| JP | 2019141015 A1 | 8/2019 |

(Continued)

OTHER PUBLICATIONS

Eng Trans of WO 0056610 A2, Frocke Heinz et al. (Year: 2000).*
Ogi et al., (WO 2011117983 A1, Eng Trans). (Year: 2011).*

*Primary Examiner* — Blessing M Fubara
(74) *Attorney, Agent, or Firm* — Christopher C. Dremann, P.C.; Christopher C. Dremann

(57) ABSTRACT

Substrates for use with an aerosol delivery device to vaporize and deliver an aerosol to a user include a base material, an aerosol former and an aerosol agent. In a method for forming the substrates, a mixture of substrate materials is extruded and then spheronized to produce pellet substrates that are generally spherical, substantially spherical or rounded, or in the form of relatively short rods having rounded ends. In another method for forming the substrates, a base material is coated with a first coating and optionally the base material having the first coating thereon is subsequently coated with a second coating so as to produce pellet substrates having a relatively smooth, dry exterior surface. In this manner, the substrates are formable relative to one another and can be easily and readily loaded into and removed from the aerosol delivery device.

20 Claims, 4 Drawing Sheets

(56) References Cited

U.S. PATENT DOCUMENTS

| | | | |
|---|---|---|---|
| 5,020,548 A | 6/1991 | Farrier et al. | |
| 5,129,409 A * | 7/1992 | White | A24B 15/165 131/84.1 |
| 5,137,034 A | 8/1992 | Perfetti et al. | |
| 5,144,962 A | 9/1992 | Counts et al. | |
| 5,388,573 A | 2/1995 | Mulhauser et al. | |
| 5,388,574 A | 2/1995 | Ingebrethsen | |
| 5,396,911 A | 3/1995 | Casey, III et al. | |
| 5,460,173 A | 10/1995 | Mulhauser et al. | |
| 6,164,287 A | 12/2000 | White | |
| 8,251,060 B2 | 8/2012 | White et al. | |
| 8,915,254 B2 | 12/2014 | Monsees et al. | |
| 8,925,555 B2 | 1/2015 | Monsees et al. | |
| 9,016,274 B1 | 4/2015 | White | |
| 9,149,072 B2 | 10/2015 | Conner et al. | |
| 9,439,453 B2 | 9/2016 | Conner et al. | |
| 10,624,386 B2 * | 4/2020 | White | A61M 11/048 |
| 2004/0099269 A1 * | 5/2004 | Hale | A61M 15/002 128/203.16 |
| 2005/0013862 A1 | 1/2005 | Tobyn et al. | |
| 2006/0157491 A1 | 6/2006 | Whittle et al. | |
| 2008/0110470 A1 | 5/2008 | Zhuang et al. | |
| 2009/0155363 A1 * | 6/2009 | Maibach | A61K 9/0056 514/777 |
| 2009/0275669 A1 | 11/2009 | Aida et al. | |
| 2010/0273217 A1 * | 10/2010 | Maestracci | C12P 19/14 435/165 |
| 2011/0232657 A1 | 9/2011 | Karles et al. | |
| 2012/0067360 A1 | 3/2012 | Conner et al. | |
| 2013/0228170 A1 | 9/2013 | Alper | |
| 2013/0255702 A1 | 10/2013 | Griffith, Jr. et al. | |
| 2014/0261486 A1 | 9/2014 | Potter | |
| 2015/0101606 A1 | 4/2015 | White | |
| 2015/0209530 A1 | 6/2015 | White | |
| 2015/0335070 A1 | 11/2015 | Sears et al. | |
| 2015/0359259 A1 | 12/2015 | Conner et al. | |
| 2016/0073695 A1 | 3/2016 | Sears et al. | |
| 2016/0219926 A1 | 8/2016 | Whiffen | |
| 2016/0295914 A1 | 10/2016 | Jordil et al. | |
| 2018/0014576 A1 | 1/2018 | White | |
| 2018/0368472 A1 | 12/2018 | Mishra et al. | |
| 2019/0269170 A1 * | 9/2019 | White | A61M 16/14 |
| 2020/0253264 A1 * | 8/2020 | Rousseau | A24B 15/165 |
| 2021/0084963 A1 | 3/2021 | Watanabe | |

FOREIGN PATENT DOCUMENTS

| | | | |
|---|---|---|---|
| WO | WO-2012177555 A2 * | 12/2012 | B82Y 30/00 |
| WO | 2017153718 A1 | 9/2017 | |
| WO | 2019069160 A1 | 4/2019 | |

* cited by examiner

SUBSTRATES FOR VAPORIZING AND DELIVERING AN AEROSOL

FIELD OF THE INVENTION

The present invention relates to substrates for vaporizing and delivering an aerosol. In exemplary embodiments, the invention is a substrate formed from a base material and an aerosol former that is configured for use with an aerosol delivery device to vaporize and deliver an aerosol, for example, an aerosol containing nicotine and/or flavoring to a smoker, or an aerosol containing a therapeutic drug to a patient.

BACKGROUND OF THE INVENTION

The adverse health risks associated with smoking cigarettes have been recognized for decades. It is estimated that at least seventy percent (70%) of smokers today desire to reduce the amount of cigarettes they smoke, or want to quit altogether. Despite the known risks, only about six percent (6%) of smokers report that they were able to quit smoking entirely. The low rate of success is believed to be due to the highly addictive nature of nicotine present in conventional cigarettes. Nicotine gum and nicotine patches for the delivery of nicotine without the harmful by products of tobacco combustion have been available for years. Nicotine gum and nicotine patches, however, have proven to be largely unsuccessful as smoking cessation articles due to their failure to satisfy the smoker's hand-to-mouth and inhalation urges. In the past, nicotine delivery devices in the form of combustion-free electronic cigarettes, referred to as "smokeless cigarettes" and "e-cigarettes," as well as atomizers, cartomizers and vaporizers (including vape pens) have been developed and introduced to the public.

Popular brands of electronic cigarettes include BLU ECIGS® offered by Lorillard Technologies, Inc. of Greensboro, N.C., USA, VUSE® offered by Reynolds Innovations, Inc. of Winston-Salem, N.C., USA, MARK 10™ offered by Phillip Morris, Inc. of Richmond, Va., USA, and NJOY® offered by NJOY, Inc. of Scottsdale, Ariz., USA. Popular brands of vaporizers include FIREFLY® offered by Firefly Company of San Francisco, Calif., USA, Matrix offered by Mig Vapor of Pompano Beach, Fla., USA, PAX® offered by PAX Labs, Inc. of San Francisco, Calif., USA, V2Pro™ offered by VMR Products, LLC of Miami, Fla., USA, HAZE® V3 offered by Haze Industries, Inc. of Atlanta Ga., USA, and IOLITE WISPR® offered by Oglesby & Butler Ltd. of Carlow, Ireland.

Each of the aforementioned commercially available electronic cigarettes and vaporizers replicates the hand-to-mouth and inhalation experiences of a traditional tobacco cigarette desired by smokers. Electronic cigarettes and vaporizers also satisfy a smoker's craving for the addictive nicotine without exposing the smoker to the carcinogenic by-products produced by the combustion of tobacco and without exposing by-standers to harmful second-hand smoke. As a result, electronic cigarettes and vaporizers are credited with providing a healthier nicotine delivery option to smokers and a healthier environment to by-standers subjected to second-hand smoke by significantly reducing, and potentially eliminating, the harmful effects of the carcinogens present in the smoke that would otherwise be produced and dispersed by lighting and smoking a traditional tobacco cigarette.

Traditional tobacco cigarettes are made of a combustible material that is ignited with a flame to cause the tobacco to burn. Burning tobacco releases smoke containing nicotine that is inhaled by the smoker to deliver the nicotine to the lungs. Electronic cigarettes, on the other hand, heat a liquid, referred to as "e-liquid" or "liquid nicotine," containing nicotine and in some instances flavoring, to convert the liquid into an aerosol. The aerosol, commonly referred to as nicotine vapor or simply vape, is inhaled by the smoker to deliver the nicotine to the lungs. Most of the current electronic cigarettes include a battery energy source, an atomizer and a re-fillable or expendable cartridge that contains the liquid nicotine. Due to the frequency required to re-fill or replace the cartridge, an advanced type of electronic cigarette has been developed that combines the atomizer and the cartridge into a single "cartomizer" electrically connected to the battery. Cartomizers allow for a greater period of time between re-fills or replacements. The vaporization process is initiated by the smoker inhaling, or alternatively, by the smoker depressing a manual switch, to activate the atomizer or cartomizer. The atomizer heats the e-liquid to convert an aerosol former, such as glycerin or propylene glycol, and the liquid nicotine into nicotine vapor (vape) in the form of an aerosol. The vape is inhaled through a mouthpiece to deliver nicotine to the lungs of the smoker. The smoker then exhales the residual nicotine vapor as cigarette smoke absent the harmful by-products of tobacco combustion. Vaporizers operate similarly to e-cigarettes with the exception that most vaporizers utilize dry herb material as the substrate that is heated to form the aerosol that is vaporized and delivered to the user.

Despite the reduced health risks, there remain certain disadvantages with the electronic cigarettes currently available. For example, the e-liquid contained within the cartridge or cartomizer typically contains a solution of propylene glycol, vegetable glycerin (VG), and/or polyethylene glycol 400 (PEG400) mixed with concentrated flavoring and a highly variable concentration of nicotine. However, the liquid nicotine solutions of some electronic cigarettes have been found to still contain cancer-causing agents, referred to as tobacco-specific nitrosamines (TSNAs), as well as tobacco-specific impurities, such as anabasine, myosmine, and ß-nicotine. In fact, a recent study by the Food and Drug Administration (FDA) detected diethylene glycol, a poisonous and hygroscopic liquid commonly used in anti-freeze solutions, in the e-liquid of an electronic cigarette, and measurable levels of nicotine in e-liquid cartridges that claimed to be nicotine-free. These findings are particularly disturbing since the cartridges and cartomizers of electronic cigarettes are inherently susceptible to leakage and/or breakage owing to their small size and relative fragility. As a result, the danger exists that a cartridge or cartomizer could leak or break and can cause a user to ingest or have skin contact with a harmful amount of the liquid solution containing nicotine. It is also possible for a leaking e-liquid to damage the electronics and/or corrode the battery of an electronic nicotine delivery device. Furthermore, the glycerin or propylene glycol aerosol forming agent in the e-liquid is a flammable liquid, and therefore, could ignite and cause a fire if the e-liquid leaks and comes into contact with an ignition source.

Likewise, there are certain disadvantages with the vaporizers that are currently available. As previously mentioned, vaporizers typically utilize a dry herb material as the substrate that is heated to form the aerosol that is vaporized and delivered to the user. The dry herb material is placed into a combination heating and aerosolizing chamber, commonly referred to as the oven. For the best result, it is essential that the dry herb material is finely ground and contains very little moisture, preferably less than about fifteen percent (15%). Accordingly, additional equipment, such as a dryer and a fine herb grinder are necessary for an optimal vaping experience. Furthermore, the vaporizers that operate on the principle of conduction heating produce better vapor when the ground dry herb material is more tightly packed in the oven. Conversely, the vaporizers that operate on the principle of convection heating produce better vapor when the dry herb material is more loosely packed in the oven. Regardless, the processes of drying, grinding and packing the dry herb material into the oven of the vaporizer, as well as subsequently removing the dry herb material residue and cleaning the oven, can be time consuming and messy, thereby making it difficult for users to have a consistently optimal vaping experience.

Therapeutic agents, and in particular therapeutic drugs, are commonly delivered to a patient, via a pill, capsule, tablet or the like that is ingested orally and absorbed into the bloodstream. A therapeutic drug may also be introduced directly into the bloodstream via an intravenous solution. Therapeutic drugs that are ingested orally and absorbed require a longer period of time before the effects of the drug are realized by the patient. Furthermore, therapeutic drugs delivered to a patient via a pill, capsule, tablet or the like suffer from a loss of effectiveness due to hepatic metabolism. Intravenous drug delivery is more effective than oral ingestion, but is generally inconvenient for a patient that is not resident in a health care facility. In addition, administration of a therapeutic drug by intravenous means can be dangerous and/or painful. Delivery of a therapeutic drug in the form of an aerosol by inhalation overcomes the disadvantages of both delivery methods, but has yet to gain widespread acceptance and use. Aerosol delivery devices for vaporizing and delivering a therapeutic drug in the form of an aerosol include atomizers, vaporizers and inhalers (including nebulizers). Inhalation formulations for use with aerosol delivery devices of therapeutic drugs are generally provided as solutions, suspensions and powders containing the therapeutic drug.

One possible reason for the limited role of inhalation drug delivery despite its increased efficacy, as well as convenient, safe and painless administration, is the lack of a suitable aerosol delivery device that is relatively easy to use for portable, reliable and repeatable vaporization and delivery of a wide variety of therapeutic drugs in an aerosol form. Existing devices for vaporizing and delivering a therapeutic drug in the form of an aerosol are suitable for use with only a limited class of therapeutic drugs, such as drugs for the treatment of asthma. In addition, none of the existing inhalation formulations for use with an aerosol delivery device to vaporize and deliver a therapeutic drug in the form of an aerosol are suitable to provide convenient, safe, reliable and effective dosage control.

Accordingly, an improved substrate is needed for vaporizing and delivering an aerosol, for example, an aerosol containing nicotine and/or flavoring to a smoker, or an aerosol containing a therapeutic drug to a patient. Furthermore, a substrate for vaporizing and delivering a wide variety of recreational and therapeutic substances in the form of an aerosol is needed that is more convenient, safe, reliable and easy to use. In particular, a substrate for vaporizing and delivering an aerosol is desired that overcomes the problems, deficiencies and disadvantages of the aerosol delivery devices and substrates that are currently available. Specifically, a substrate for vaporizing and delivering a wide variety of substances in the form of an aerosol is needed that eliminates the risk of damaging the electronics or power source of an aerosol delivery device, or igniting and causing a fire. Further, such a substrate should not require the use of additional equipment, time or effort to prepare the substrate and to clean the aerosol delivery device, so as to provide a consistently enjoyable vape or inhalation experience. A substrate for vaporizing and delivering a therapeutic drug in the form of an aerosol is also needed that provides convenient, safe, reliable and effective dosage control.

As used herein, the term "aerosol" is intended to include vapors, gases, fine particles, and the like, both visible and invisible, generated by a heat source acting upon a substrate for forming an aerosol in a manner consistent with the present invention. As so defined, the term "aerosol" specifically includes pharmacologically or physiologically active agents and any desired additives, such as an aerosol forming agent (also referred to herein as an "aerosol former"), flavoring, etc. irrespective of whether a visible aerosol is produced. As used herein, the term "in heat conducting relation" is intended to mean a physical arrangement of two or more components whereby heat is transferred by conduction or convection from a heat generating source (e.g. a heating element) to a thermally conductive component (e.g. a heat conductor or directly to a substrate) substantially throughout the heat generating period of the heat source. A heat conducting relation can be achieved by locating the components in direct physical contact or in close proximity to one another, or alternatively, by fluid (e.g. air) convection with one another during operation of the heat source.

BRIEF DESCRIPTION OF THE DRAWINGS

These and other features, aspects and advantages of the invention are better understood and appreciated when considered in light of the following detailed description of the invention with reference to the accompanying drawings.

DETAILED DESCRIPTION OF EXEMPLARY EMBODIMENTS

Figure 1:
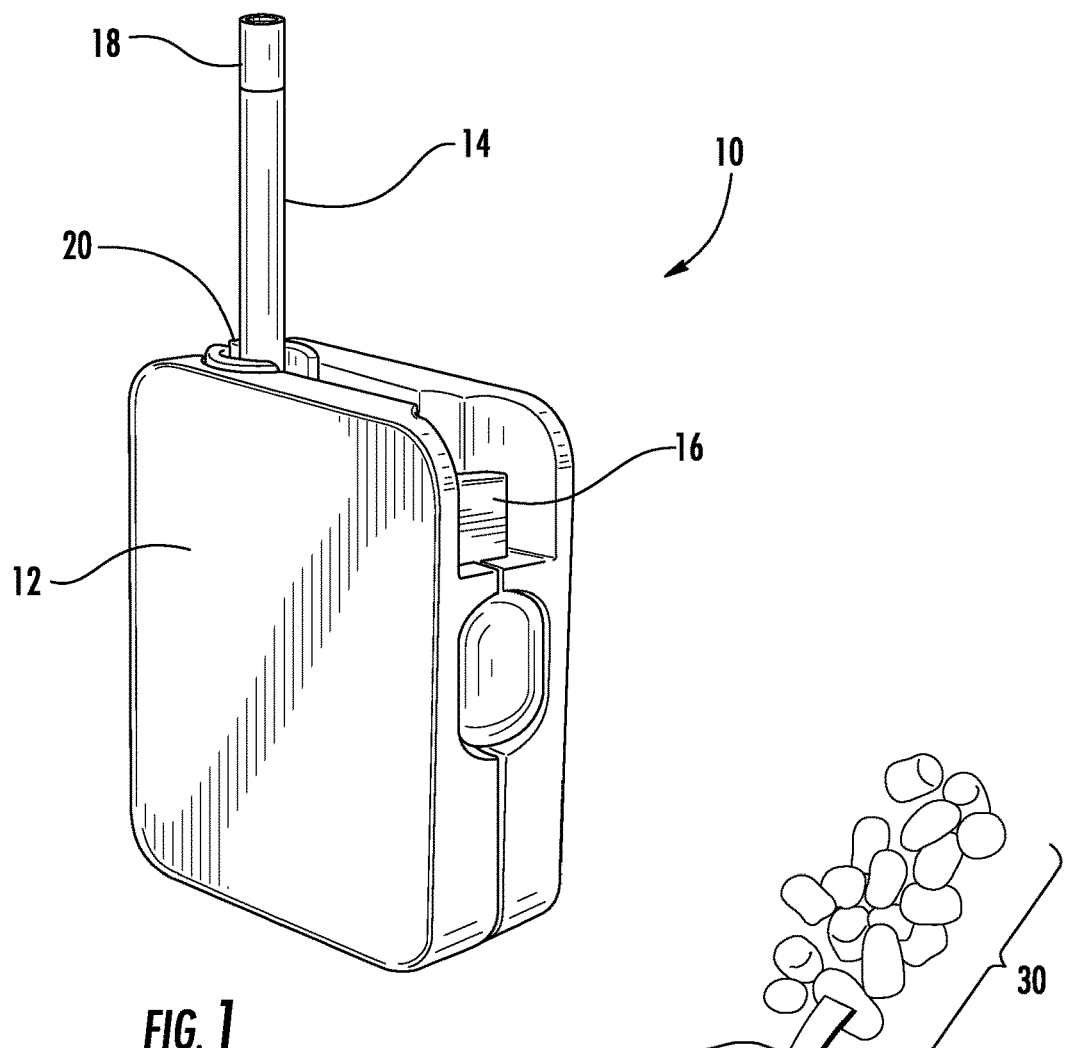
FIG. 1 is a perspective view of a conventional aerosol delivery device suitable for use with substrates for vaporizing and delivering an aerosol according to the invention.

The invention will be described more fully hereinafter with reference to the accompanying drawing figures in which exemplary embodiments of the invention are shown. However, it is to be understood that the invention may be embodied in many different forms and should not be construed as limited to the exemplary embodiments set forth herein. Exemplary embodiments of the invention are described herein so that this disclosure will completely and accurately convey the full scope of the invention and thereby enable one of ordinary skill in the art to make, use and practice the invention without undue experimentation Like reference characters in the written description and accompanying drawing figures refer to the same or similar parts, elements, assemblies and/or systems of the invention.

The exemplary embodiments of the invention show and describe substrates for vaporizing and delivering a substance in the form of an aerosol. As used herein, the term "aerosol" is intended to include vapors, dense gases, fine suspended particles, and the like, both visible and invisible. As such, "aerosol" and "aerosol agent" specifically include any pharmacologically or physiologically active agents, and any desired additives, including by way of example, an aerosol former, nicotine, a flavoring, a therapeutic drug, tetrahydrocannabinol (THC), cannabidiol (CBD), etc. Preferably, but not necessarily, the aerosol has a density consistent with cigarette smoke and a small particle size on the order of about 0.2-3.0 microns. As used herein, the term "aerosol nicotine" refers to nicotine in the form of an aerosol delivered to a smoker from an aerosol delivery device, such as a combustion-free, heat-without-burn or heat-not-burn (HNB) electronic cigarette, vape pen, atomizer, cartomizer, vaporizer or the like. Similarly, as used herein, the term "aerosol drug" refers to a therapeutic compound or therapeutic drug in the form of an aerosol delivered to a patient from an aerosol delivery device, such as an atomizer, vaporizer or inhaler (including a nebulizer). The aerosol agent, and more specifically the aerosol nicotine or the aerosol drug, is preferably formed by an aerosol former activated by heat generated by a heat generator, for example a heating element, and conducted by a heat conductor. In certain instances, the heat generator and the heat conductor may be one and the same component. An aerosol delivery device suitable for use with substrates for vaporizing and delivering an aerosol or aerosol agent according to the invention provides a portable, convenient, safe, reliable, easy to use and effective system for reliably and repeatedly vaporizing and delivering an aerosol and a wide variety of aerosol agents to a user. By way of example and not limitation, such aerosol delivery devices are particularly useful for vaporizing and delivering nicotine and/or flavoring to a smoker, or a therapeutic drug to a patient.

Figure 2:
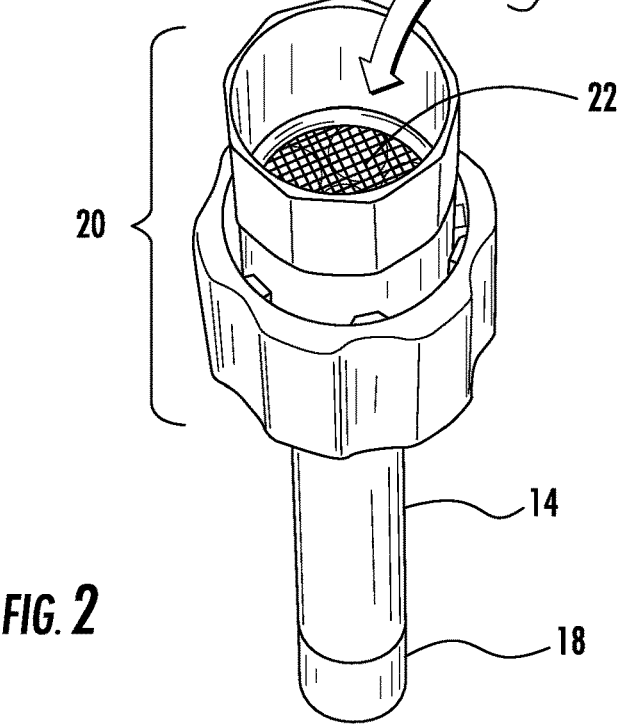
FIG. 2 is a perspective view showing substrates for vaporizing and delivering an aerosol according to the invention being loaded into the aerosol delivery device of FIG. 1.

An aerosol delivery device, indicated generally by reference character 10, suitable for use with a substrate for vaporizing and delivering an aerosol agent according to the present invention is shown in FIG. 1. By way of example and not limitation, a suitable aerosol delivery device 10 is commercially known as IOLITE WISPR® and is available from Oglesby & Butler Ltd. of Carlow, Ireland. The device 10 comprises a housing 12, an aerosol delivery chamber 14 extending outwardly from the housing 12 in the form of a generally hollow tube or stem, and an actuator 16 for activating the device between an inactive mode, an initial heating mode and a subsequent aerosol delivery mode. The device 10 may further comprise a removable mouthpiece (not shown) that is attached to the free end 18 of the aerosol delivery chamber 14 for delivering the aerosol agent in the form of an aerosol to a user. Conversely, the mouthpiece may be formed as an extension of the aerosol delivery chamber 14. FIG. 2 shows a heating and vaporizing chamber 20 of the aerosol agent delivery device 10. The heating and vaporizing chamber 20 is also commonly referred to as the "oven" of the device 10. Oven 20 is constructed so as to be in fluid (i.e., air) communication with the aerosol delivery chamber 14 and is removably disposed within the housing 12 of the device 10.

In FIG. 2, the oven 20 is shown removed from the housing 12 of the device 10 and inverted in position for being loaded with substrates, indicated generally by reference character 30, according to the invention. Thus, the oven 20 additionally functions as a substrate holder for the substrates 30. As illustrated herein, the oven 20 comprises a mesh screen 22 for preventing the substrates 30 from being drawn through the aerosol delivery chamber 14 and the mouthpiece to the user. The aerosol delivery device 10 may further comprise a heat conductor (not shown) disposed within the housing 12 for preventing the substrates 30 from coming into direct contact with a heat generator or heating element (not shown) of the device. The heating element may be powered by an electrical power source (e.g. battery) or a combustible gas (e.g. butane) power source in a known manner and as shown and described in U.S. Pat. No. 9,016,274 B1, the entire disclosure of which is incorporated herein by reference.

The substrates 30 are formed from a base material that easily conforms to the size and shape of the heating and vaporizing chamber 20 of the aerosol delivery device 10. As previously mentioned, an aerosol delivery device 10 suitable for use with the substrates 30 is the IOLITE WISPR® vaporizer commercially available from Oglesby & Butler Ltd. of Carlow, Ireland. However, other suitable devices exist, including: the handheld IOLITE® vaporizer, likewise available from Oglesby & Butler Ltd.; the PAX® and PAX 2® handheld vaporizers available from PAX Labs, Inc. of San Francisco, Calif., USA; the VOLCANO™ desktop vaporizer available from the Storz & Bickel Company of Tuttlingen, Germany; the FIREFLY® handheld vaporizer available from Firefly Company of San Francisco, Calif., USA; the IQOS® tobacco heating system (THS) available from Phillip Morris International (PMI) of New York, N.Y., USA; the glo® tobacco heating product (THP) available from British American Tobacco (BAT) of London, UK; and numerous others. Each of the aforementioned aerosol delivery devices has a heating and vaporizing chamber that is configured to receive, or to be adapted to receive, substrates 30 according to the invention. In particular, the substrates 30 can be easily deposited into the heating and vaporizing chamber, for example by pouring or funneling, and can be easily and readily removed after use without leaving an undesirable residue. In that regard, it has been determined that substrates 30 having a generally spherical, substantially spherical, somewhat rounded or rod-like with rounded ends shape are particularly advantageous for filling and emptying the heating and vaporizing chambers of most aerosol delivery devices. In addition, a substrate 30 having a generally spherical, substantially spherical, rounded or rod-like with rounded ends shape provides additional surface area for volatizing (vaporizing) an aerosol former and an aerosol agent from a base material of the substrate.

In one embodiment, the substrate 30 has a relatively short, rod-like shape. Preferably, the rods have rounded ends and a length that is only about 2-4 times the diameter of the rod. By way of example and not limitation, a substrate 30 in the shape of a relatively short rod with rounded ends may have a diameter of between about 0.5 mm and about 2 mm, and a length of between about 1 mm and about 4 mm. As will be readily understood and appreciated by those skilled in the art, a shorter length of the rod is preferable for pouring the substrates 30 into the heating and vaporizing chamber with the substrates 30 conforming to the size and shape of the heating and vaporizing chamber. Furthermore, as the length of the rod is reduced, the shape of the substrate 30 approaches a generally spherical, substantially spherical or rounded shape, and therefore, increases the surface area of the substrate 30 available for vaporization of the aerosol former and/or aerosol agent. For substrates 30 having a generally spherical or substantially spherical shape, a range of diameters between about 0.5 mm and about 3 mm is preferred. It has been found that substrates 30 having a diameter of between about 1 mm and about 2 mm appear to provide an optimal combination of pouring (loading), removing (unloading) and heat transfer characteristics. For purposes of this written description of exemplary embodiments of the invention, substrates 30 having the aforementioned generally spherical, substantially spherical, rounded or rod-like shape are referred to as "pellet shaped substrates" or "pellet substrates."

Substrates 30 according to the invention can be formed by several different methods and may be formed from numerous different base materials and/or mixtures of base materials. Exemplary embodiments of suitable methods and suitable base materials are disclosed and shown herein. However, it will be understood and appreciated by those skilled in the art that equivalent methods and materials, as well as others not specifically disclosed herein, are to be encompassed by the intended broad scope of the invention. By way of example and not limitation, suitable base materials for forming substrates 30 include cellulose-based, starch-based and sugar-based substances and inorganic powders, such as calcium carbonate, alumina, carbon, etc. In particular embodiments, the base material of the substrate 30 may comprise an organic fiber, such as food fiber or plant fiber, or a grain, such as millet, rice, corn, wheat, sorghum, rye, etc. In some instances it may be advantageous or necessary to coat the base material with a hydrocolloid binding agent or binder, such as sodium carboxymethylcellulose (NaCMC), guar gum, xanthan gum, an alginate or the like.

Figure 3:
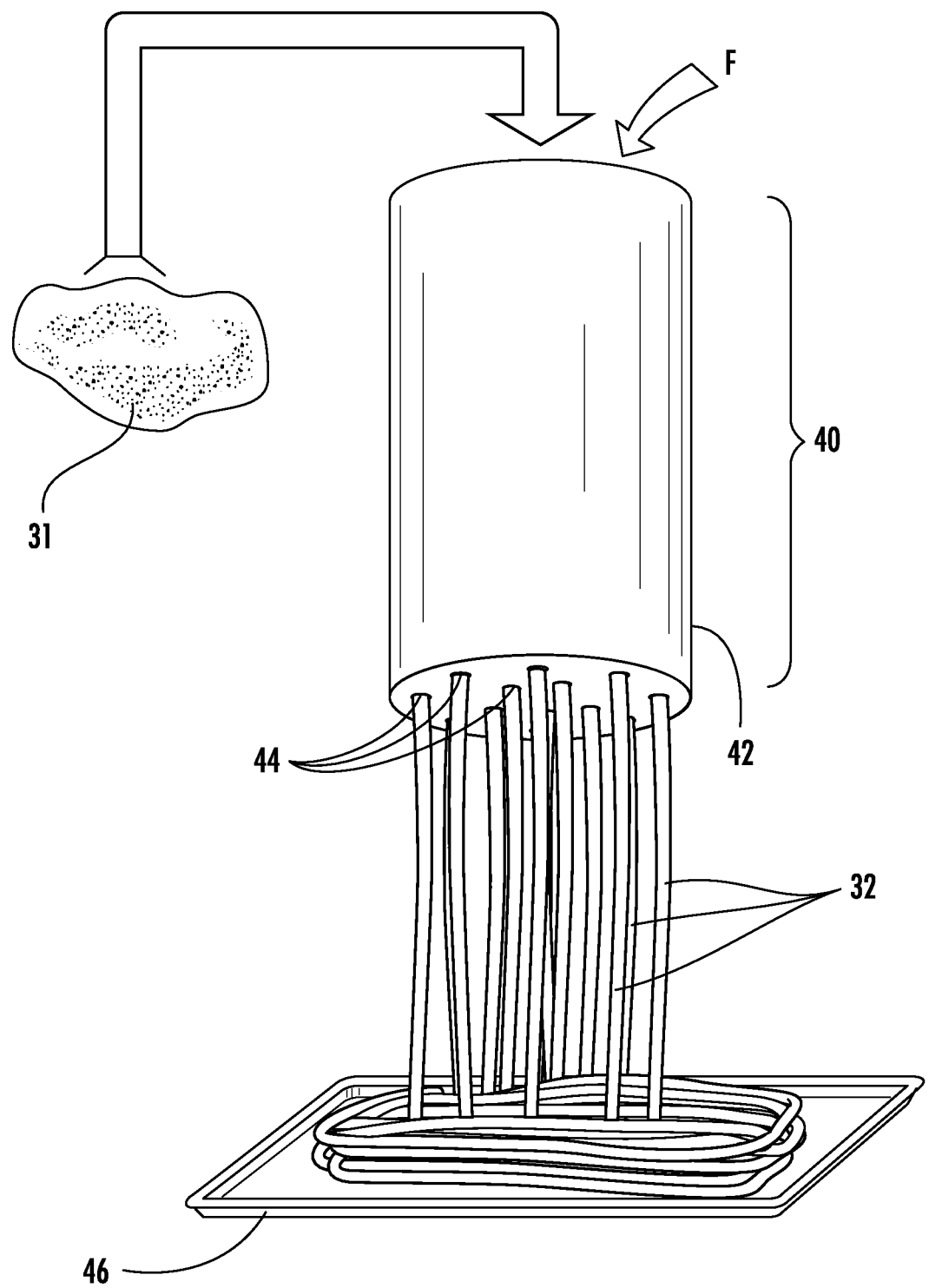
FIG. 3 is a perspective view showing a conventional extruder for forming substrates for vaporizing and delivering an aerosol according to the invention in a method according to the invention.

An exemplary embodiment of a first method for forming substrates 30 according to the invention comprises extruding a mixture of substrate materials 31 and spheronizing elongate lengths (referred to herein as strands) of the extruded substrate materials into generally spherical, substantially spherical or rounded shapes, or into relatively short length rods having rounded ends. By way of example and not limitation, the mixture of substrate materials 31 may comprise a base material of an organic fiber (e.g. food fiber, plant fiber, etc.) mixed together with an aerosol former and an aerosol agent (e.g., nicotine, tobacco powder, tobacco extract, therapeutic drug, flavoring, etc.). If necessary, water may be added in an amount sufficient to form a semi-liquid or viscous paste suitable for extrusion. FIG. 3 shows a conventional extruder, indicated generally by reference character 40, for extruding substrate materials to subsequently form substrates 30 for vaporizing and delivering an aerosol agent to a user in the form of an aerosol. The extruder 40 is utilized in a first step of a method for forming a substrate 30 according to the invention. As shown herein, the extruder 40 comprises an elongate, generally cylindrical extrusion tube 42 having a plurality of lengthwise through holes 44. A semi-viscous mixture of at least one substrate material 31 is fed into the extrusion tube 42 of the extruder 40 in any suitable manner. A compression force F is then applied to the mixture of the substrate material 31 inside the extrusion tube 42 such that a plurality of elongate strands 32 of the substrate material 31 exit the extruder 40 through the corresponding plurality of through holes 44 and are collected onto a collection tray 46.

Figure 4:
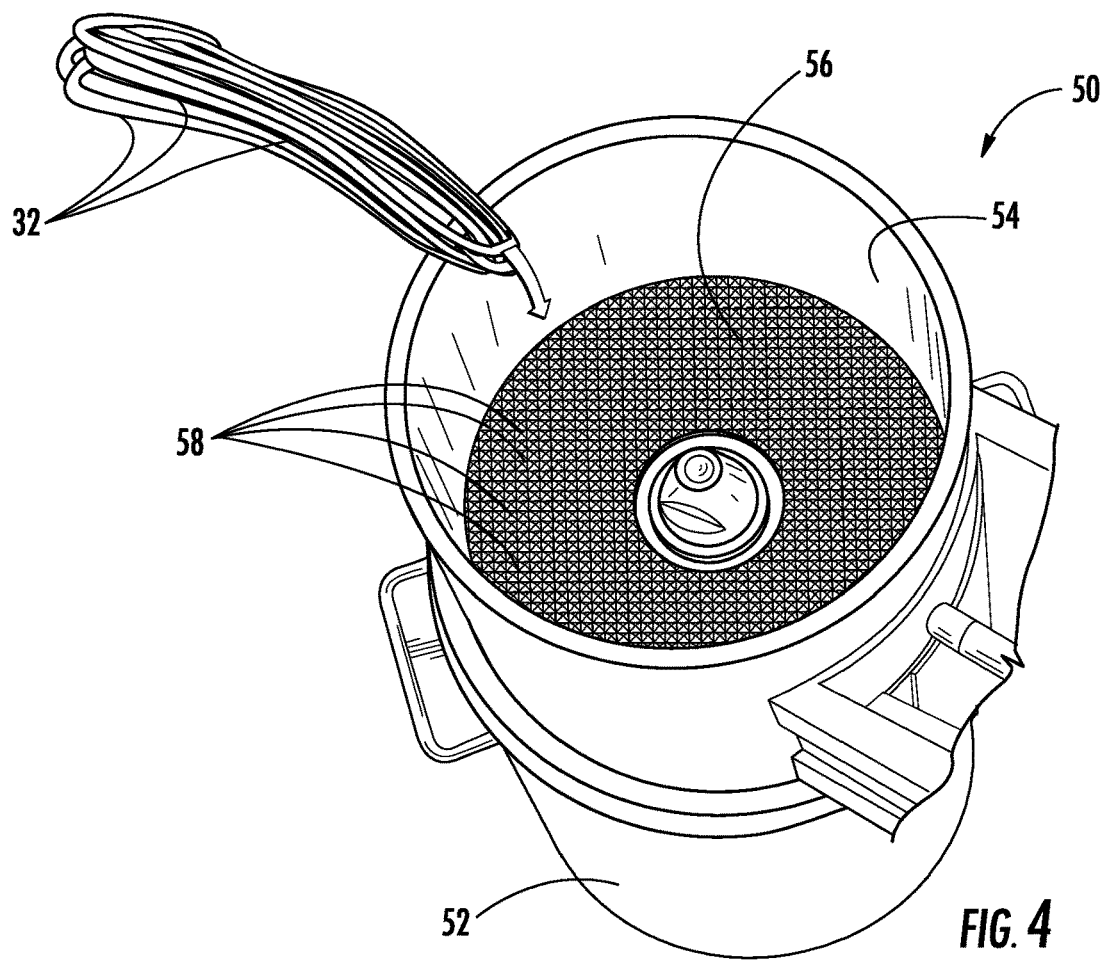
FIG. 4 is a perspective view showing a conventional spheronizer for forming substrates for vaporizing and delivering an aerosol according to the invention in a method according to the invention.

FIG. 4 shows a conventional spheronizer, indicated generally by reference character 50, for forming substrates 30 for vaporizing and delivering an aerosol agent to a user in the form of an aerosol. The spheronizer 50 is utilized in a second step of a method for forming substrates 30 according to the invention. As shown herein, spheronizer 50 comprises a generally hollow, cylindrical drum 52 defining an open interior compartment 54 configured for receiving the substrate material 31 of the substrates 30. Spheronizer 50 further comprises a generally circular spheronizing plate 56 defining a plurality of generally pyramid-shaped or tooth-shaped protrusions 58 on the spheronizing plate 56. The spheronizer 50 further comprises a motor (not shown) for rotating the spheronizing plate 56 relative to the drum 52 about a common longitudinal axis of the drum 52 and the spheronizing plate 56.

Figure 5:
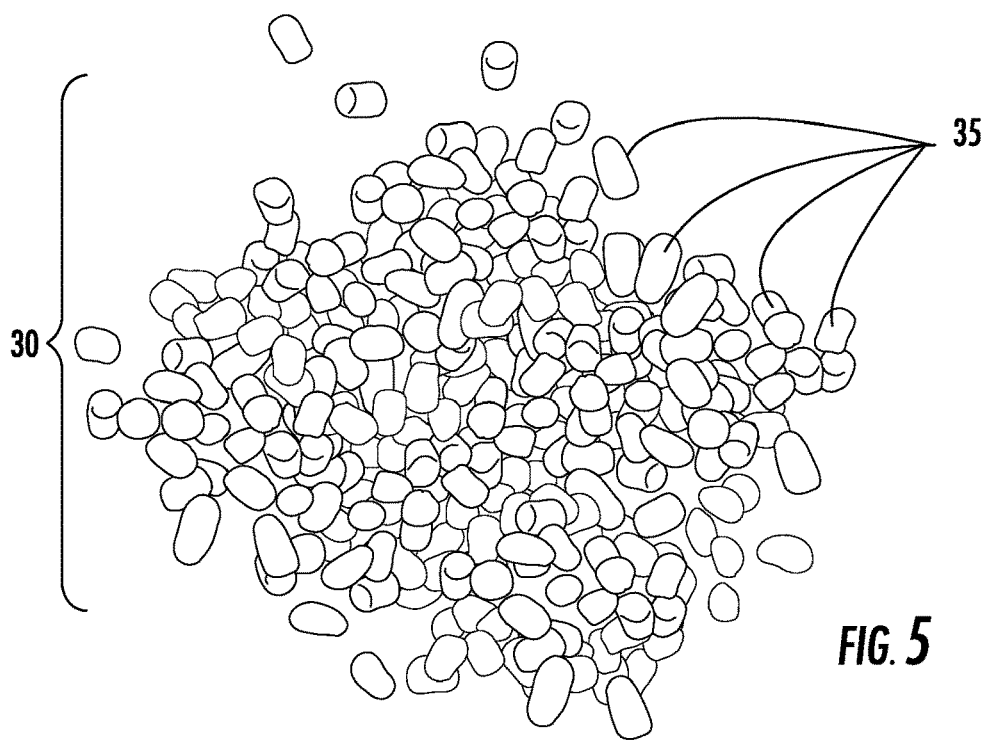
FIG. 5 is a perspective view showing substrates for vaporizing and delivering an aerosol according to the invention.

In one embodiment, strands 32 of the substrate material 31 extruded by the extruder 40 in the first step of the method are introduced into the drum 52 onto the spheronizing plate 56 of the spheronizer 50 in any suitable manner. Spheronizing plate 56 is then rotated about the longitudinal axis such that the protrusions 58 cut and chop the strands 32 of the substrate material 31 into generally spherical, substantially spherical or rounded shapes or into relatively short length rods having rounded ends that form a plurality of individual pellet substrates 35, as shown in FIG. 5. If desired, the spheronizing plate 56 may be oscillated in a lengthwise direction so as to further engage the strands 32 of the substrate material 31 and thereby reduce their size and/or enhance the shape of the pellet substrates 35.

In another embodiment, a substrate material 31 of a substrate 30 that is already in the form of a generally spherical, substantially spherical or rounded shape or a relatively short rod-like shape can be spheronized using the spheronizer 50 in essentially the same manner as previously described to produce pellet substrates 35 having a smaller size or an enhanced shape.

As previously mentioned, numerous different substrate materials 31 and mixtures of substrate materials 31 may be utilized to form substrates 30 according to the invention by the methods described herein. In one embodiment, such a method comprises mixing one or more dry ingredients, an aerosol former and a hydrated water soluble gum binder. The aerosol former is added to the dry ingredients and mixed thoroughly with the dry ingredients. The hydrated water soluble gum binder is then added and mixed thoroughly with the dry ingredients and the aerosol former. The moisture content of the mixture is then adjusted to obtain a mixture having a suitable consistency for being extruded. Alternatively, the dry ingredients, aerosol former and water soluble gum binder can be mixed thoroughly and water added to form a paste suitable for extrusion. Regardless, the mixture is then extruded, for example using the extruder 40 in the manner previously described, and if desired spheronized, for example using the spheronizer 50 in the manner previously described. Finally, the generally spherical, substantially spherical, or rounded pellet substrates 35, or the relatively short rods having rounded ends that constitute the pellet substrates 35, are dried as necessary and packaged for subsequent use in an aerosol delivery device 10 of the type previously described.

The following examples of substrate materials 31 and mixtures of substrate materials 31 have been found to be particularly well suited for forming pellet substrates 35 according to the invention using a method according to the invention. In general, a mixture of substrate materials 31 comprises a base material that is ground into a fine powder, an aerosol former and a hydrocolloid water soluble gum. If necessary, water may be added in a sufficient amount to form an extrudable paste. The mixture of substrate materials 31 or the extrudable paste is then extruded to produce strands 32 of the mixture of substrate materials 31. The extruded strands 32 of the substrate materials 31 may then be spheronized to form pellet substrates 35 of a desired size and shape.

Example 1 is a mixture of substrate materials 31 comprising peppermint leaf, glycerin and sodium carboxymethylcellulose (NaCMC 7LF). The peppermint leaf was ground into a fine powder and about 200 grams of the peppermint powder was mixed with about 50 grams of the glycerin and about 2.5 grams of the NaCMC 7LF. Water was then added in an amount sufficient to form an extrudable paste. The paste was extruded through a die plate having a plurality of 1.6 mm diameter orifices. The resulting extruded strands 32 of the mixture of substrate materials 31 were then spheronized into pellet substrates 35. About 300 mg of the peppermint-based pellet substrates 35 were loaded into an aerosol delivery device 10, and specifically, into the butane fuel IOLITE WISPR® vaporizer, and heated to about 190° C. When drawing on the aerosol delivery device 10, the peppermint-based pellet substrates 35 generated a substantial volume of visible aerosol. The aerosol generated by the peppermint-based pellet substrates 35 had an excellent menthol and tobacco cigarette smoke taste. The tobacco cigarette smoke taste was an entirely unexpected result since the peppermint-based pellet substrates 35 did not contain any tobacco or nicotine, and there was no combustion of the pellet substrates 35.

Example 2 is a mixture of substrate materials 31 comprising hemp biomass shucked from stalk, glycerin and sodium carboxymethylcellulose (NaCMC 7LF). The hemp biomass was ground into a fine powder and about 200 grams of the hemp powder was mixed with about 50 grams of the glycerin and about 1.25 grams of the NaCMC. Water was then added in an amount sufficient to form an extrudable paste. The paste was extruded through a die plate having a plurality of 1.6 mm diameter orifices. The resulting extruded strands 32 of the mixture of substrate materials 31 were then spheronized into pellet substrates 35. About 300 mg of the hemp-based pellet substrates 35 were loaded into an aerosol delivery device 10, and specifically, into the butane fuel IOLITE WISPR® vaporizer, and heated to about 190° C. When drawing on the aerosol delivery device 10, the hemp-based pellet substrates 35 generated a good volume of visible aerosol. The aerosol generated by the hemp-based pellet substrates 35 had a pleasant taste, which was an entirely unexpected result.

Example 3 is a mixture of substrate materials 31 comprising about 19.6% of an aerosol former, such as glycerin; about 38.3% of calcium carbonate; about 30.4% of a cellulose fiber (VITACEL C-601); about 0.98% of carboxymethylcellulose (CMC 7LF); and about 10.6% of calgon carbon grade PCB. This composition of substrate materials 31 produces pellet substrates 35 constituting relatively short rods having rounded ends, which may be spheronized in addition as desired.

Example 4 is a mixture of substrate materials 31 comprising about 20% of an aerosol former, such as glycerin; about 20% of a cellulose fiber (VITACEL C-601); about 40% of calcium carbonate; about 2% of Calgon BGHHM carbon; and about 18% corn starch. This composition of substrate materials 31 produces pellet substrates 35 constituting relatively short rods having rounded ends, which may be spheronized in addition as desired.

Example 5 is a mixture of substrate materials 31 comprising about 40% of an apple fiber (VITACEL AF 400); about 40% of calcium carbonate; about 20% of an aerosol former, such as glycerin; and about 0.5% of carboxymethylcellulose (CMC 7LF). This composition of substrate materials 31 produces pellet substrates 35 constituting relatively short rods having rounded ends, which may be spheronized in addition as desired.

Example 6 is a mixture of substrate materials 31 comprising about 0.5% of carboxymethylcellulose (CMC 7LF); about 40% of an oat fiber (VITACEL HF550-30); about 40% of calcium carbonate; and about 20% of an aerosol former, such as glycerin. This composition of substrate materials 31 produces pellet substrates 35 constituting spheres and relatively short rods having rounded ends, which may be spheronized in addition as desired.

Example 7 is a mixture of substrate materials 31 comprising about 0.5% of carboxymethylcellulose (CMC 7LF); about 40% of a vanilla bean fiber (VAF 405); about 40% of calcium carbonate; and about 20% of an aerosol former, such as glycerin. This composition of substrate materials 31 produces pellet substrates 35 constituting spheres and relatively short rods, which may be spheronized in addition as desired.

Example 8 is a mixture of substrate materials 31 comprising about 0.5% of carboxymethylcellulose (CMC 7LF); about 36.2% of a ground coffee; about 32% of calcium carbonate; about 20.1% of an aerosol former, such as glycerin; and about 11.5% of a vanilla bean fiber (VAF 405).

Example 9 is a mixture of substrate materials 31 comprising about 0.5% of carboxymethylcellulose (CMC 7LF); about 40% of an apple fiber (VITACEL AF 401); about 40% of calcium carbonate; and about 20% of a menthol flavor mixture comprising about 70% glycerin, about 30% propylene glycol and about 1% nicotine.

Example 10 is a mixture of substrate materials 31 comprising about 0.5% of carboxymethylcellulose (CMC 7LF); about 40% of a potato fiber (KF 200); about 40% of calcium carbonate; and about 20% of an aerosol former, namely glycerin containing about 10% nicotine and about 2.5% peppermint oil.

It will be readily understood and appreciated by those skilled in the art that the foregoing examples are not exclusive or exhaustive and numerous others not expressly disclosed herein are within the intended scope of the invention. In particular, it should be noted that practically all food type fibers (e.g. cocoa bean, chocolate bean, tea, etc.) may be utilized as a substrate material 31 that is ground into a powder and extruded in a mixture of substrate materials 31. The resulting strands 32 of extruded substrate materials 31 optionally may then be spheronized to produce generally spherical, substantially spherical, rounded or rod-like shaped pellet substrates 35.

Figure 6B:
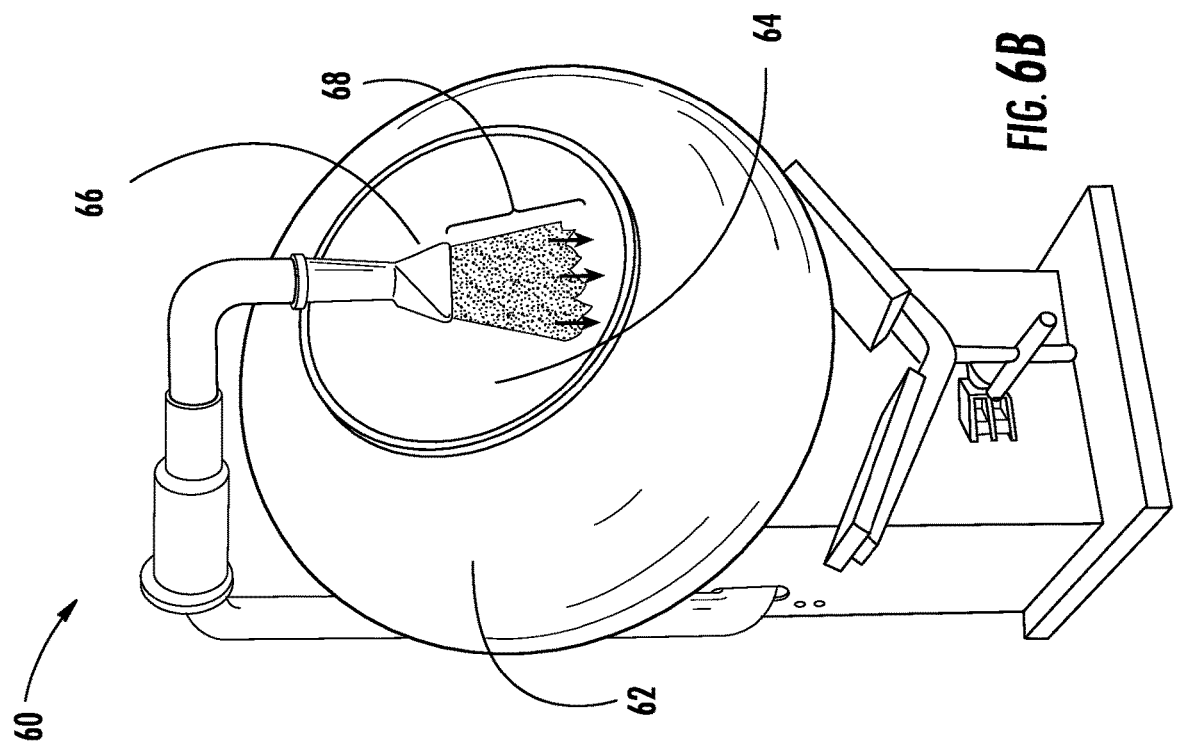
FIG. 6B is a perspective view showing the coating drum of FIG. 6A for forming substrates for vaporizing and delivering an aerosol according to the invention in another method according to the invention.
Figure 6A:
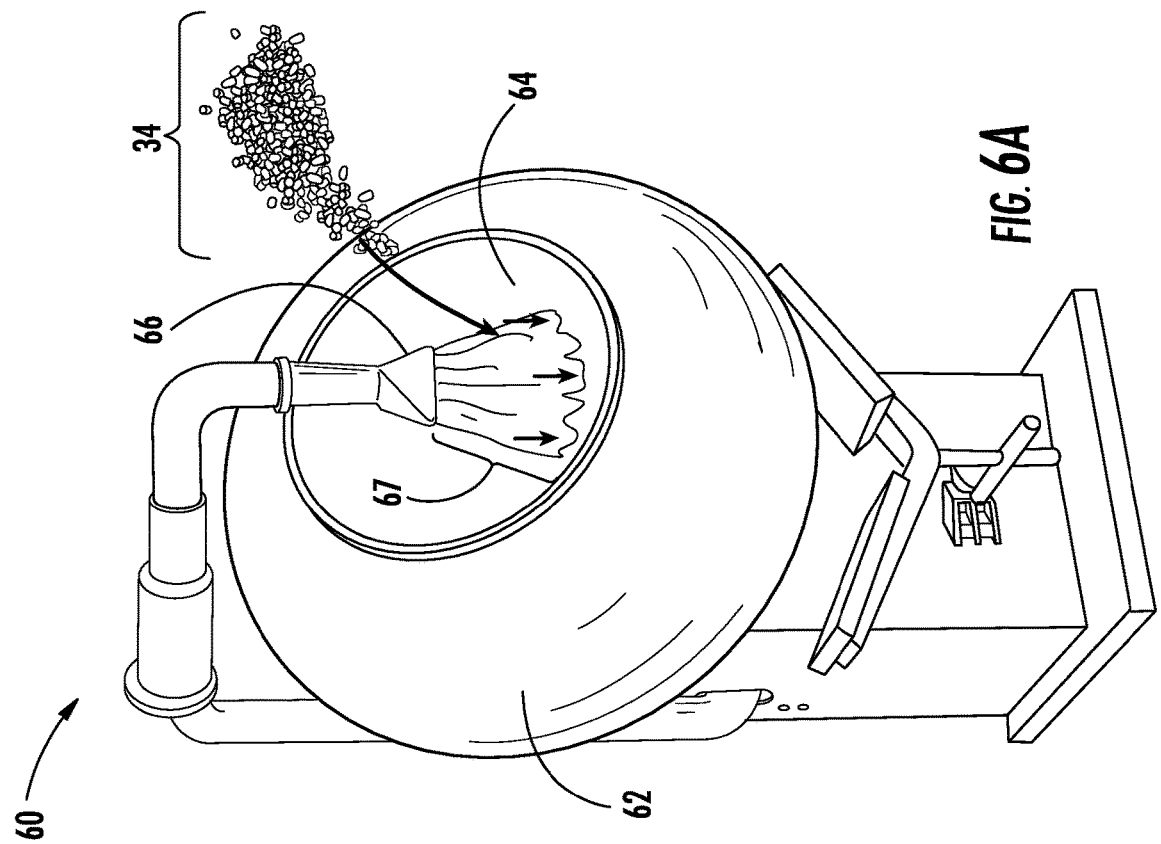
FIG. 6A is a perspective view showing a conventional coating drum for forming substrates for vaporizing and delivering an aerosol according to the invention in another method according to the invention.

Another exemplary embodiment of a method for forming substrates 30 according to the invention comprises initially coating a carrier material, referred to herein as a base material, with a first coating comprising an aerosol forming agent (aerosol former) and an aerosol agent, preferably in the form of a liquid, and optionally coating the base material having the first coating thereon with a second coating comprising an inorganic powder or a hydrocolloid, preferably in the form of a dry solid. In advantageous embodiments, the base material is inherently generally spherical, substantially spherical or rounded, or rod-like in the shape of relatively short rods having rounded ends. FIG. 6A and FIG. 6B show a conventional coating machine or coater, indicated generally by reference character 60, suitable for use with this method for forming substrates 30 for vaporizing and delivering an aerosol to a user. The coater 60 is preferably the type of rotating coating machine that is used in the preparation of coated candies, medicine pills and the like. Regardless, the coater 60 forms the substrates 30 from a base material, indicated generally by reference character 34, by coating the base material 34 with the first coating and optionally coating the base material 34 having the first coating thereon with the second coating.

As shown herein, the coater 60 comprises a hollow, generally cylindrical rotatable coating drum 62 defining an open interior compartment 64 for receiving the base material 34. The coater 60 further comprises a dispensing arm/dispensing nozzle 66 configured for introducing a coating substance into the interior compartment 64 of the coating drum 62. The coater 60 further comprises a motor (not shown) for rotating the coating drum 62 relative to the dispensing arm/dispensing nozzle 66 about a central axis (not shown) of the coating drum 62. As shown herein, the central axis of the coating drum 62 is inclined relative to horizontal by about thirty degrees (30°).

The method comprises loading, for example by feeding or pouring, the base material 34 into the interior compartment 64 of the coating drum 62 in any suitable manner. The method further comprises using the dispensing arm/dispensing nozzle 66 to introduce, for example by spraying, an initial or first coating, indicated generally by reference character 67 in FIG. 6A, into the interior compartment 64 of the drum 62. Preferably, the first coating 67 is in the form of a wet liquid or a semi-viscous liquid. The method optionally further comprises using the dispensing arm/dispensing nozzle 66 to introduce, for example by feeding, a subsequent or second coating, indicated generally by reference character 68 in FIG. 6B, into the interior compartment 64 of the drum 62. Preferably, the second coating 68 is in the form of a dry solid or a dry semi-solid. The plurality of pellet substrates 35, as shown in FIG. 5, may be produced by the base material 34 coated with the first coating 67, or alternatively, by the base material 34 coated with the first coating 67 subsequently coated with the second coating 68.

In general, a base material 34 having a suitable size and shape is selected. The base material 34 may be any suitable thermally stable material having sufficient surface area and/or porosity to retain an aerosol forming agent and an aerosol agent, and furthermore, to permit aerosol formation by vaporization with the application of heat. As used herein, "thermally stable" is intended to mean capable of withstanding the relatively high temperatures (e.g. about 180° C. to about 600° C.) present within the heating and vaporizing chamber 20 of the aerosol delivery device 10. The base material 34 may be generally spherical, substantially spherical or rounded, or is rod-like in the form of relatively short rods having rounded ends. Regardless, the base material 34 has an aggregate diameter of about 0.5 mm to about 3 mm and an aggregate length of about 1 mm to about 4 mm. In a particularly advantageous embodiment, the base material 34 has a diameter of about 2 mm to about 3 mm. If necessary, the size of the base material 34 may be reduced, for example by grinding, chopping or the like. Alternatively, or in addition, the base material 34 may be screened to obtain individual substrates of a desired size and/or shape, for example sieved to about 8-20 mesh.

The base material 34 is loaded, for example by feeding or pouring, into the interior compartment 64 defined by the coating drum 62. The coating drum 62 is rotated as the dispensing arm/dispensing nozzle 66 introduces the first coating 67 into the interior compartment 64 of the coating drum 62 so that the base material 34 is thoroughly and evenly coated with the first coating 67. Typically, the first coating 67 comprises at least an aerosol forming agent, such as glycerin, vegetable glycerin (VG), propylene glycol, polyethylene glycol or mixtures thereof, and an aerosol agent, such as nicotine, a therapeutic drug (e.g. aspirin), THC or CBD oil, etc. in a liquid form. If desired, the first coating 67 may further comprise a flavor additive, such as menthol, chocolate, cocoa, vanilla, peppermint, etc. The base material 34 with the first coating 67 applied may then be allowed to dry so as to allow a liquid first coating to be absorbed, adsorbed or adhered onto the base material 34 to a suitable extent.

In some instances, it may necessary or desired to provide the base material 34 having the first coating 67 thereon with the second coating 68. In such instances, the coating drum 62 is again rotated as the dispensing arm/dispensing nozzle 66 introduces the second coating 68 into the interior compartment 64 of the coating drum 62 so that the base material 34 having the first coating 67 thereon is thoroughly and evenly coated with the second coating 68. Typically, the second coating 68 comprises a relatively inert inorganic powder, such as calcium carbonate, aluminum oxide, alumina, carbon or the like, and combinations thereof, or alternatively, a hydrocolloid water soluble gum, such as NaCMC, CMC, guar gum, xanthan gum, an alginate, or the like, and combinations thereof, in the form of a dry solid. The inorganic powder or the hydrocolloid water soluble gum of the dry solid second coating 68 serves to bind (adhere) the liquid first coating 67 to the surface of the base material 34. As a result, the second coating 68 provides a relatively smooth, dry surface on the pellet substrates 35. Thus, pellet substrates 35 produced by this method of the invention flow relative to one another for easily and readily filling and removing the pellet substrates 35 from the heating and vaporizing chamber (oven) 20 of the aerosol delivery device 10. In addition, the second coating 68 may reduce dusting, cracking, fracturing and/or off-gassing of the pellet substrates 35.

The following examples of combinations of a base material 34, a first coating 37 and a second coating 38 have been found to be particularly well suited for forming pellet substrates 35 according to the invention using a method according to the invention. In general, the base material 34 is inherently generally spherical, substantially spherical, rounded, or rod-like in the form of relatively short rods having rounded ends. However, the base material 34 may be further formed to a desired shape and size. For example, the base material 34 may be ground and screened or sieved to about 8-20 mesh. Regardless, the base material 34 is received within an interior compartment 64 of a coating drum 62. A first coating comprising at least an aerosol former and an aerosol agent is introduced into the interior compartment 64 of the coating drum 62 and the coating drum 62 rotated so that the base material 34 is coated with the first coating 67. A second coating 68 comprising an inorganic powder or a hydrocolloid water soluble gum may be introduced into the interior compartment 64 of the coating drum 62 and the coating drum 62 rotated so that the base material 34 with the first coating 67 thereon is coated with the second coating 68. The base material 34 coated with the first coating 67, or alternatively, the base material 34 coated with the initial first coating 67 and the subsequent second coating 68, form the pellet substrates 35 according to the invention.

Example 11 is a base material 34 in the form of a grain that is ground as necessary and sieved to about 8-20 mesh. Grains of the type suitable for the base material 34 include millet, rice, corn, wheat, sorghum, rye, etc. Millet grains are naturally of a desired size, and therefore, do not require grinding. Among the suitable grains, millet and rice grains are preferred since they typically will not contribute to the taste of the aerosol produced by the pellet substrates 35. Regardless, the grains of the base material 34 are coated with a first coating 67 comprising at least an aerosol former and an aerosol agent, preferably in the form of a liquid. The aerosol former may comprise, for example, propylene glycol, glycerin and combinations thereof. The aerosol agent may comprise, for example, nicotine, tobacco extract, tobacco powder, flavoring (e.g. menthol, peppermint, chocolate, cocoa, vanilla, etc.), a therapeutic drug, a therapeutic compound, THC or CBD oil and combinations thereof.

The first coating 67 is absorbed, adsorbed or adhered onto the exterior surface of the grains of the base material 34. Preferably, however, the grains of the base material 34 are puffed so that the first coating 67 is absorbed, adsorbed or adhered on the interstices of the puffed grain in addition to the exterior surface. The increased absorbance of the puffed grains results in a greater amount of aerosol former and aerosol agent of the first coating 67 applied to the grains of the base material 34. Thus, the pellet substrates 35 produce a more concentrated aerosol for the same weight of the grains of the base material 34. In some instances, the grains of the base material 34 with the first coating 67 of aerosol former and aerosol agent applied thereon is coated with a second coating 68 comprising an inorganic powder or a hydrocolloid water soluble gum binder, preferably in the form of a dry solid. As previously mentioned, the hydrocolloid water soluble gum may, for example, be NaCMC, CMC, guar gum, xanthan gum, an alginate or combinations thereof. In general, grains of the base material 34 that are not puffed (also referred to as unpuffed) have liquid aerosol former on the exterior surface, and therefore, may require a second coating 68 of inorganic powder or hydrocolloid to provide a dry exterior surface. On the other hand, grains of the base material 34 that are puffed absorb, adsorb or adhere the liquid aerosol former internally within the interstices, and therefore, do not require a second coating 68 of inorganic powder or hydrocolloid, unless for improved taste or enhanced delivery of a therapeutic drug. Regardless, the optional second coating 68 is absorbed, adsorbed or adhered onto the exterior surface and any interstices of the grains of the base material 34 coated with the first coating 67.

Example 12 is a base material 34 that is coated with a first coating 67 comprising a therapeutic drug or therapeutic compound. The base material 34 may be activated carbon, activated alumina or a grain. Activated carbon and puffed millet grains are preferred as the base material 34 for applying a first coating 67 of a therapeutic drug or therapeutic compound due to the porous structure of the activated carbon and the interstices formed within the millet grains by the puffing process. Puffed rice grains are also preferred, but may need to be ground and sized. Other grains can be puffed to provide additional interstices, however, puffed millet grains and puffed rice grains are less likely to contribute to an undesirable taste of the aerosol produced by the pellet substrates 35. The therapeutic drug or therapeutic compound may be any suitable pharmaceutical, nicotine, THC, CBD, etc. For purposes of this example, the therapeutic drug or therapeutic compound is aspirin.

A base material 34 of puffed millet grains in an amount of 40.0 grams (69.4% by weight) was introduced into an interior compartment 64 of a rotating coating drum 62 of a conventional coater 60. A first coating 67 comprising aspirin in the amount of 1.625 grams (2.8% by weight) dissolved in 20 grams of ethanol was applied slowly to the puffed millet grains of the base material 34 within the interior compartment 64 of the rotating coating drum 62 until the first coating 67 was well absorbed onto the base material 34. The ethanol was allowed to gradually dry and/or evaporate from the puffed millet grains of the base material 34. A second coating 68 comprising a mixture of propylene glycol in an amount of 10 grams (17.4% by weight) and glycerin in an amount of 6 grams (10.4% by weight) was applied to the puffed millet grains of the base material 34 coated with the first coating 67 of aspirin in the interior compartment 64 of the rotating coating drum 62 until the second coating 68 was well absorbed onto the base material 34 having the first coating 67 thereon. A sample of the pellet substrates 35 produced by the foregoing example was loaded into an aerosol delivery device 10, and specifically, into the butane fuel IOLITE WISPR® vaporizer, and heated to about 190° C. When drawing on the aerosol delivery device 10, the millet grain/aspirin-based pellet substrates 35 generated a good volume of visible aerosol. The aerosol generated by the millet grain/aspirin-based pellet substrates 35 had a pleasant sweet taste, which was an entirely unexpected result.

Example 13 is a composition of a base material 34 comprising about 64.5% of a Davinci Acini Di Pepe wheat pasta; a first coating 67 comprising about 16.1% of an aerosol former, such as glycerin; and a second coating 68 comprising about 19.4% of calcium carbonate. This composition of the base material 34, the liquid first coating 67 and the dry solid second coating 68 produces pellet substrates 35 constituting generally spherical, substantially spherical and/or rounded shapes.

Example 14 is a composition of a base material 34 comprising about 72.7% of an organic orzo Whole Foods brand wheat pasta; a first coating 67 comprising about 18.1% of an aerosol former, such as glycerin; and a second coating 68 comprising about 9.1% of calcium carbonate. This composition of the base material 34, the liquid first coating 67 and the dry solid second coating 68 produces pellet substrates 35 constituting generally spherical, substantially spherical and/or rounded shapes.

Example 15 is a composition of a base material 34 comprising about 72.7% of a Tinkyada white rice pasta of the spaghetti style; a first coating 67 comprising about 18.1% of an aerosol former, such as glycerin; and a second coating 68 comprising about 9.1% of calcium carbonate. This composition of the base material 34, the liquid first coating 67 and the dry solid second coating 68 produces pellet substrates 35 constituting generally spherical, substantially spherical and/or rounded shapes.

Example 16 is a composition of a base material 34 comprising about 40% of puffed millet grains; a first coating 67 comprising about 20% of an aerosol former, such as glycerin; and a second coating 68 comprising about 40% of calcium carbonate. This composition of the base material 34, the liquid first coating 67 and the dry solid second coating 68 produces pellet substrates 35 constituting generally spherical, substantially spherical and/or rounded shapes.

Example 17 is a composition of a base material 34 comprising about 64% of an American Basmati white rice; a first coating 67 comprising about 16% of an aerosol former, such as glycerin; and a second coating 68 comprising about 20% of calcium carbonate. This composition of the base material 34, the liquid first coating 67 and the dry solid second coating 68 produces pellet substrates 35 constituting generally spherical, substantially spherical and/or rounded shapes.

Example 18 is a composition of a base material 34 comprising about 76.5% of a short grain white rice of the sushi style; a first coating 67 comprising about 18.9% of an aerosol former, such as glycerin; and a second coating 68 comprising about 5.6% of calcium carbonate. This composition of the base material 34, the liquid first coating 67 and the dry solid second coating 68 produces pellet substrates 35 constituting generally spherical, substantially spherical and/or rounded shapes.

Example 19 is a composition of a base material 34 comprising about 71.4% of steel cut oats; a first coating 67 comprising about 17.9% of an aerosol former, such as glycerin; and a second coating 68 comprising about 10.7% of calcium carbonate. This composition of the base material 34, the liquid first coating 67 and the dry solid second coating 68 produces pellet substrates 35 constituting generally spherical, substantially spherical and/or rounded shapes.

Example 20 is a composition of a base material 34 comprising about 69% of hulled millet grains; a first coating 67 comprising about 17.2% of an aerosol former, such as glycerin; and a second coating 68 comprising about 13.8% of calcium carbonate. This composition of the base material 34, the liquid first coating 67 and the dry solid second coating 68 produces pellet substrates 35 constituting generally spherical, substantially spherical and/or rounded shapes.

Example 21 is a composition of a base material 34 comprising about 67.6% of hulled millet grains; a first coating 67 comprising a mixture of about 6.8% of an aerosol former, such as glycerin, and about 6.8% of a flavoring comprising about 87.5% glycerin, about 2.5% peppermint oil and about 10% nicotine; and a second coating 68 comprising about 18.8% of calcium carbonate. This composition of the base material 34, the liquid first coating 67 and the dry solid second coating 68 produces pellet substrates 35 constituting generally spherical, substantially spherical and/or rounded shapes.

Example 22 is a composition of a base material 34 comprising about 73.5% of a short grain white rice of the sushi style; a first coating 67 comprising a mixture of about 7.4% of an aerosol former, such as glycerin, and about 7.4% of a flavoring comprising about 87.5% glycerin, about 2.5% peppermint oil and about 10% nicotine; and a second coating 68 comprising about 11.7% of calcium carbonate. This composition of the base material 34, the liquid first coating 67 and the dry solid second coating 68 produces pellet substrates 35 constituting generally spherical, substantially spherical and/or rounded shapes.

Example 23 is a composition of a base material 34 comprising about 62.5% of a roasted buckwheat; a first coating 67 comprising about 15.6% of a tobacco flavor e-liquid mixture comprising about 70% glycerin, about 30% propylene glycol and about 1% nicotine; and a second coating 68 comprising about 21.9% of calcium carbonate. This composition of the base material 34, the liquid first coating 67 and the dry solid second coating 68 produces pellet substrates 35 constituting generally spherical, substantially spherical and/or rounded shapes.

Example 24 is a composition of a base material 34 comprising about 62.5% of hulled millet grains; a first coating 67 comprising about 15.6% of a mazing mocha flavor e-liquid mixture comprising about 70% glycerin, about 30% propylene glycol and about 0.3% nicotine; and a second coating 68 comprising about 21.9% of calcium carbonate. This composition of the base material 34, the liquid first coating 67 and the dry solid second coating 68 produces pellet substrates 35 constituting generally spherical, substantially spherical and/or rounded shapes.

Example 25 is a composition of a base material 34 comprising about 62.5% of hulled millet grains; a first coating 67 comprising about 15.6% of a tobacco flavor e-liquid mixture comprising about 70% glycerin, about 30% propylene glycol and about 1% nicotine; and a second coating 68 comprising about 21.9% of calcium carbonate. This composition of the base material 34, the liquid first coating 67 and the dry solid second coating 68 produces pellet substrates 35 constituting generally spherical, substantially spherical and/or rounded shapes.

Example 26 is a composition of a base material 34 comprising about 62.5% of hulled millet grains; a first coating 67 comprising about 15.6% of an e-liquid mixture comprising about 70% glycerin, about 30% propylene glycol and about 1% nicotine with menthol; and a second coating 68 comprising about 21.9% of calcium carbonate. This composition of the base material 34, the liquid first coating 67 and the dry solid second coating 68 produces pellet substrates 35 constituting generally spherical, substantially spherical and/or rounded shapes.

Example 27 is a composition of a base material 34 comprising about 58.8% of hulled millet grains; a first coating 67 comprising a mixture of about 14.7% of an aerosol former, such as glycerin, and about 11.8% of a tobacco powder; and a second coating 68 comprising about 14.7% of calcium carbonate. The first coating 67 of the tobacco powder mixed with the aerosol former was coated onto the base material 34 of hulled millet grains, and then the second coating 68 of the dry solid calcium carbonate was coated onto the base material 34 of hulled millet grains having the first coating 67 of the mixture of aerosol former and tobacco powder thereon so as to provide a dry exterior surface. Furthermore, any excess tobacco powder was screened off of the hulled millet grains base material 34. This composition of the base material 34, the liquid first coating 67 and the dry solid second coating 68 produces pellet substrates 35 constituting generally spherical, substantially spherical and/or rounded shapes.

It will be readily understood and appreciated by those skilled in the art that the foregoing examples are not exclusive or exhaustive and numerous others not expressly disclosed herein are within the intended scope of the invention. In particular, it should be noted that practically all food types having a generally granular form may be utilized as a base material 34 that is coated with a first coating 67, or alternatively, an initial first coating 67 and a subsequent second coating 68. The resulting compositions of base material 34, first coating 67 and optional second coating 68 produce pellet substrates 35 constituting generally spherical, substantially spherical and/or rounded shapes.

Specific substances, components, elements, materials and mixtures suited for use with the methods according to the invention for forming substrates according to the invention include, but are not limited to, the following:

a) Cellulose gum comprising sodium carboxymethylcellulose, type 7LF available from Ashland Aqualon Functional Ingredients, Inc. of Wilmington, Del., USA;

b) Calcium carbonate 5970 available from Specialty Minerals, Inc.;

c) Cellulose fibers available from J. Rettenmaier USA;

d) Water soluble food grade gums;

e) Aerosol forming agents in solid, semisolid, or liquid form, including polyhydric alcohols and mixtures of polyhydric alcohols, such as glycerin, vegetable glycerin (VG), glycerol, polyethylene glycol (PEG400), propylene glycol, 1,3-butylene glycol, triethylene glycol, glycerol esters, such as triacetin, propylene carbonate, and mixtures thereof, as well as aliphatic esters of mono-, di-, or poly-carboxylic acids, such as methyl stearate, dimethyl dodecandioate, dimethyl tetradecandioate, and others;.

f) Hydrocolloids, including agar, alginate, arabinoxylan, carrageenan, curdlan, gelatin, gellan, β-glucan, guar gum, gum arabic, locust bean gum, pectin, xanthan gum, methyl cellulose, carboxymethyl cellulose (CMC), sodium CMC, ethyl cellulose, ethyl methyl cellulose and hydroxypropyl cellulose;

g) Commercialized starches, including cornstarch, tapioca, wheat, rice, potato starch (e.g. sweet potato starch), sago mung bean and Florida arrowroot;

h) Functionalized starches, including dextrin, acid-treated starch, alkaline-treated starch, bleached starch, oxidized starch, enzyme-treated starch, monostarch phosphate, distarch phosphate, phosphated distarch phosphate, acetylated distarch phosphate, starch acetate, acetylated distarch adipate, hydroxypropyl starch, hydroxypropyl distarch phosphate, hydroxypropyl distarch glycerol, starch sodium octenyl succinate and acetylated oxidized starch;

i) organic plant material, for example, tobacco, coffee, tea, chocolate, cocoa, vanilla, peppermint, etc., in a whole, cut, chopped, ground or powder form, and plant extracts, such as a tobacco extract;

j) therapeutic drugs and therapeutic compounds, for example, pharmaceuticals, nicotine, aspirin, THC, CBD, etc.; and k) filler material, for example calcium carbonate, alumina (synthetically produced aluminum oxide), activated carbon powder, graphite powder, combinations thereof, and other similar inorganic materials that will not ignite or burn at the vaporization temperatures of the aerosol agent and aerosol forming agent.

The foregoing description of exemplary embodiments of the inventions is provided for the purposes of explanation and illustration only. Although exemplary embodiments of substrates for vaporizing and delivering an aerosol and methods for forming substrates for vaporizing and delivering an aerosol have been described herein with reference to the accompany drawing figures, various other embodiments of the inventions may exist or become later known that perform similar functions and/or achieve similar results. All such equivalents are within the spirit and intended scope of the inventions, and thus, are intended to fall within the broadest reasonable interpretation of the appended claims consistent with the specification as understood by one having ordinary skill in the relevant art.

That which is claimed is:

1. Substrates for use with an aerosol delivery device to vaporize and deliver an aerosol, comprising:
    a mixture in the form of an extrudable paste comprising an uncoated base material and an aerosol former;
    wherein the uncoated base material comprises an organic fiber that is ground into a powder before being mixed with the aerosol former; and
    wherein the extrudable paste is extruded to form rod-like substrates having a length that is about 2-4 times a diameter of the rod-like substrates, the diameter is from about 0.5 mm to about 2 mm, and the length is from about 1 mm to about 4 mm.

2. Substrates according to claim 1, wherein the substrates formed by extruding the extrudable paste are formed into short rods having rounded ends.

3. Substrates according to claim 1, wherein the substrates are spheronized after the extrudable paste is extruded.

4. Substrates according to claim 1, wherein the organic fiber is selected from the group consisting of a food fiber and a plant fiber.

5. Substrates according to claim 4, wherein the organic fiber of the base material is selected from the group consisting of a hemp biomass and a peppermint leaf.

6. Substrates according to claim 1, wherein the aerosol former is selected from the group consisting of glycerin, vegetable glycerin, and mixtures thereof.

7. Substrates according to claim 1, wherein the mixture further comprises a hydrocolloid.

8. Substrates according to claim 7, wherein the hydrocolloid comprises a hydrated water-soluble gum.

9. Substrates according to claim 1, wherein the mixture further comprises an aerosol agent in the form of a dissolved aspirin.

10. Substrates according to claim 1, wherein the mixture further comprises an aerosol agent in the form of a tetrahydrocannabinol (THC) oil, a cannabidiol (CBD) oil, or mixtures thereof.

11. Process for producing substrates according claim 1 for use with an aerosol delivery device to vaporize and deliver an aerosol, comprising:
    grinding an uncoated base material comprising an organic fiber into a powder;
    mixing the powder of the base material with an aerosol former into a mixture in the form of an extrudable paste;
    extruding the paste of the mixture to form rod-like substrates.

12. Process according to claim 11 further comprising forming the extruded substrates into short rods having rounded ends.

13. Process according to claim 11 further comprising spheronizing the extruded substrates to form spherical, substantially spherical or rounded substrates.

14. Process according to claim 11, wherein the organic fiber is selected from the group consisting of a food fiber and a plant fiber.

15. Process according to claim 11, wherein the base material is selected from the group consisting of hemp biomass and peppermint leaf.

16. Process according to claim 11, wherein the aerosol former is selected from the group consisting of glycerin, vegetable glycerin and mixtures thereof.

17. Process according to claim 11, wherein the mixture further comprises a hydrocolloid.

18. Process according to claim 17, wherein the hydrocolloid comprises a hydrated water-soluble gum.

19. Process according to claim 11, wherein the mixture further comprises an aerosol agent selected from the group consisting of a dissolved aspirin, a THC oil, a CBD oil, and mixtures thereof.

20. Substrates for delivering an aerosol, comprising:
    a base material comprising an organic fiber selected from the group consisting of a hemp biomass and a peppermint leaf that is ground into a powder;
    an aerosol former selected from the group consisting of glycerin, vegetable glycerin, and mixtures thereof; and
    an aerosol agent selected from the group consisting of a dissolved aspirin, a tetrahydrocannabinol (THC) oil, a cannabidiol (CBD) oil, or mixtures thereof;

wherein the base material, the aerosol former and the aerosol agent are mixed together to form an extrudable paste;

wherein the extrudable paste is extruded into SA-eft-rods having rounded ends to form the substrates; and wherein the rods have a length that is about 2-4 times a diameter of the rods, the diameter is from about 0.5 mm to about 2 mm, and the length is from about 1 mm to about 4 mm.

\